United States Patent [19]
Plewes

[11] Patent Number: 4,875,226
[45] Date of Patent: Oct. 17, 1989

[54] X-RAY MACHINE

[75] Inventor: Donald B. Plewes, Rochester, N.Y.

[73] Assignee: University of Rochester, Rochester, N.Y.

[21] Appl. No.: 184,210

[22] Filed: Apr. 21, 1988

[51] Int. Cl.⁴ .............................................. G21K 5/10
[52] U.S. Cl. ..................................... 378/146; 378/99
[58] Field of Search .................................. 378/146, 99

[56] References Cited
U.S. PATENT DOCUMENTS
3,766,387 10/1973 Heffan .................................. 378/146

Primary Examiner—Craig E. Church
Attorney, Agent, or Firm—Cooper & Dunham

[57] ABSTRACT

In a shadowgraphic x-ray machine the beam scans the image plane in raster fashion. A fore collimator system varies the beam cross-section during the scan to ensure that the beam footprint does not vary with position in the image plane.

10 Claims, 3 Drawing Sheets

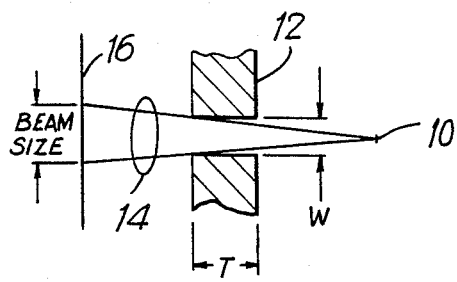
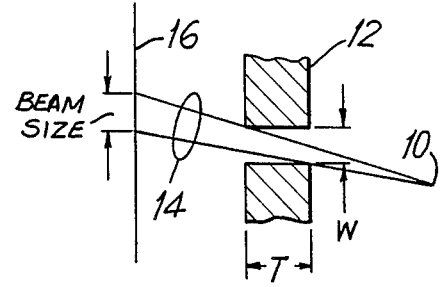
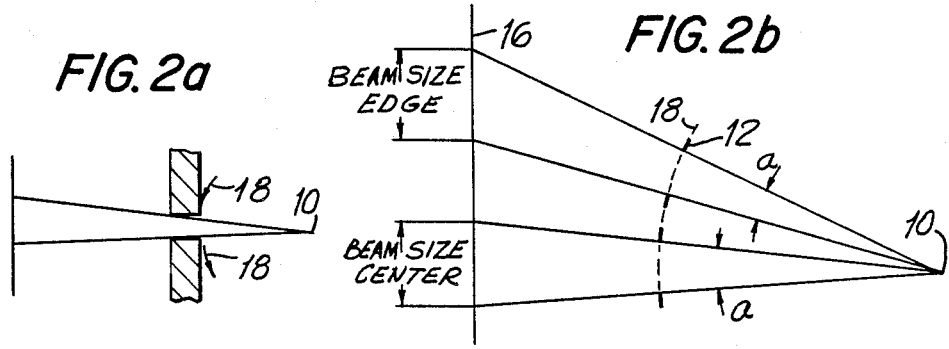
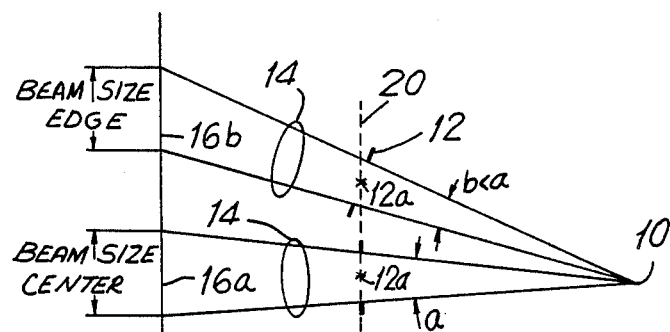

X-RAY MACHINE

BACKGROUND AND SUMMARY OF THE INVENTION

The invention is in the field of examining objects with penetrating radiation such as x-rays, and pertains to scanning an image plane with a beam to form a shadowgraphic image. An important aspect of the invention is to control the beam cross-section during the scan such that the beam footprint does not vary significantly in area with position in the image plane.

In one type of an x-ray machine a scanning x-ray beam passes through an object and scans an image plane in raster fashion. The result is a shadowgraphic x-ray image of the object's interior. Several variants of such an x-ray machine are described in the copending application of the inventor herein, filed on Apr. 14, 1986 and assigned Ser. No. 851,252, which is hereby incorporated by reference in this specification as though fully set forth herein. Further background material is found in the prior art cited in said copending application.

When scanning a beam by means of an apertured collimator, as in the prior art, the area of the beam footprint on the image plane changes during the scan. The term "footprint" is used here to refer to the area of the image plane irradiated at any one time by the scanning beam, disregarding scattered radiation. The term "scanning beam" is used here to refer to a beam of penetrating radiation which has been shaped, as by a collimator, such that it has a selected cross-sectional shape, for example a few mm square or a rectangle of a few mm on one side and a few mm to a few cm on the other.

Referring to FIGS. 1a and 1b for an illustration (not to scale), in FIG. 1a the x-rays emanating from x-ray focal spot 10 are collimated by collimator 12 into a scanning beam 14 which impinges on image plane 16. Such a collimator is sometimes called a fore collimator, meaning that it is between the source and the object plane, to distinguish it from the aft collimator which is sometimes used between the object position and the image plane. As collimator 12 moves up in the plane of the FIG. its angle with respect to central ray of beam 14 changes, for example to the angle illustrated in FIG. 1b. The footprint of beam 14 on image plane 16 is less in area in FIG. 1b than in FIG. 1a, assuming that its dimension in the direction perpendicular to the plane of the drawing remains the same. The change in footprint depends on the thickness T of collimator 12 and on the angle of central ray of beam 14 relative to collimator 12. In a typical case of a medical x-ray machine using a tantalum collimator 12 at thickness T=1 mm and a focal spot-to-collimator distance of about 12 inches, the footprint can vary by about 6%.

This change in footprint area during a scan can introduce errors, because the central part of the image plane would receive more x-ray exposure than it should. For example, if the scanning beam has a substantially constant square cross-section when entering the collimator, its footprint area would be greater at the center of the scanline and for scanlines at the center of the image plane (assuming the scanning beam is normal to the image plane at its center). If the scanning beam is rectangular, with its small dimension in the direction of the scan, and has a long dimension equal to the corresponding dimension of the image plane, the beam footprint area would be greater at the center of the image plane in the scanning direction.

In addition, in a scanning structure such as illustrated in FIGS. 1a and 1b, the size of the focal spot can vary with position of the footprint along the scan line, because different parts of the x-ray cone would be used at different times. This can introduce additional errors.

One proposal for reducing such errors is to pivot the fore collimator about the x-ray focal spot. The scanning beam thus would maintain a fixed angle to the fore collimator, and the same focal spot would be used throughout the scan. However, this would still cause error, because the footprint area would still vary with position in the image plane, albeit due to another mechanism. In a particular x-ray machine, this variation can be about 1.5%. This proposal is illustrated in FIGS. 2a and 2b, where collimator 12 moves along a curved line 18, as though it is pivoted at focal spot 10, and keeps the same angle with the central ray of scanning beam 14.

An improved way to further reduce or eliminate such errors, in accordance with one embodiment of the invention, is to not only pivot the fore collimator about the focal spot of the x-ray source but also to vary its distance from the focal spot and thereby to vary its cross-sectional area in order to keep the beam footprint on the image plane from changing in area during the scan. Stated differently, this aspect of the invention pertains to controlling the scan such that the footprint area does not change substantially with position in the image plane. In one embodiment, the collimator pivots about the focal spot and maintains its angle to the scanning beam while moving generally along a straight path. In another, the movement is along a curved path, to further reduce errors or to completely eliminate them.

Brief Description of the Drawings

FIGS. 1a and 1b illustrate a prior art technique of scanning an x-ray beam across an image plane.

FIGS. 2a and 2b illustrate another prior art scanning technique.

FIG. 3 illustrates a scanning technique in accordance with one embodiment of the invention.

DETAILED DESCRIPTION

Figure 4:
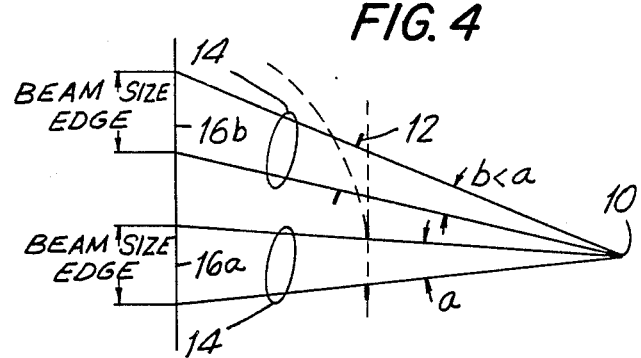
FIG. 4 illustrates a scanning technique in accordance with another embodiment of the invention.

Referring to FIG. 3, in one embodiment of the invention collimator 10 still pivots about focal spot 10, and still maintains the same angle to the central ray of scanning beam 14 as in FIGS. 1a–2b, but this time the motion is along a straight path 20 rather than along curved path 18. A central point 12a of collimator 12 is always in a plane which contains path 20 and is parallel in this case to image plane 16 (and normal to a line connecting focal spot 10 and the center of image plane 16). This varies the distance between collimator 12 and focal spot 10 during the scan—it is less at the center 16a of image plane 18 than at its edge 16b. The variation in footprint area is reduced significantly as compared with the known prior art, although not eliminated. In a particular x-ray machine it can be reduced to a level between 0.8% and 1.5%.

In a preferred embodiment of the invention, the variation in footprint with position in the image plane is substantially eliminated—by modifying the FIG. 3 embodiment to increase the variation in distance between focal spot 10 and collimator 12 as illustrated in FIG. 4.

Referring to FIG. 4, in the preferred embodiment of the invention central point 12a of collimator 12 moves along a path 22 which curves away from focal spot 10. The curvature is calculated on the basis of a number of factors to ensure that the footprint area of scanning beam 14 would not change with position in image plane 16. These factors include the size of the aperture in collimator 12 which defines scanning beam 14 and the distance from focal spot 10 to collimator 12 and image plane 16 along a line normal to image plane 16.

Figure 5A:
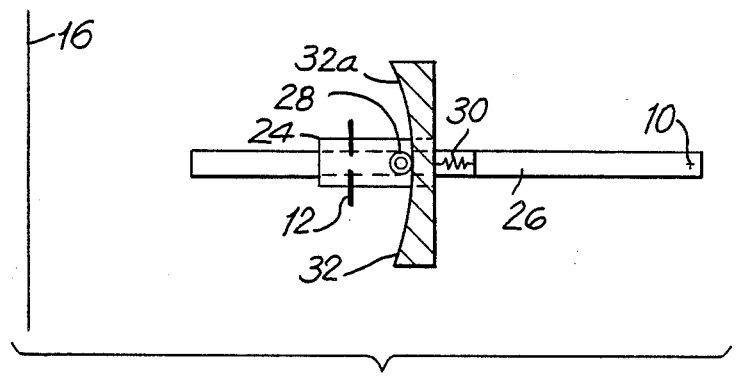
FIGS. 5a and 5b illustrate a scanning mechanism implementing the embodiment of FIG. 4.
Figure 5B:
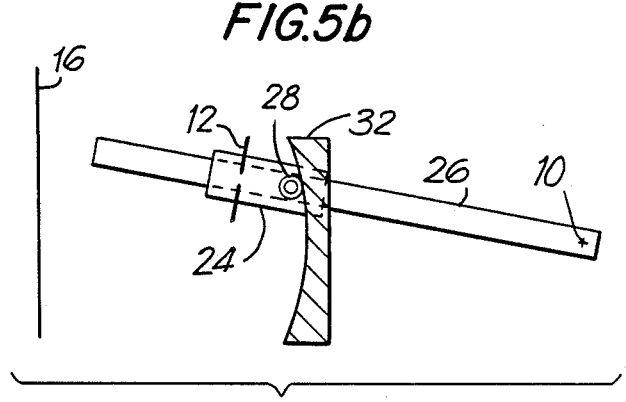

FIGS. 5a and 5b illustrate one implementation of the principle illustrated in FIG. 4. Collimator 12 is affixed to a linear bearing 24, which slides coaxially on a shaft 26 mounted to pivot about x-ray focal spot 10. Affixed to linear bearing 24 is a roller bearing 28, which is urged by a spring 30 against a curved surface 32a of a cam 32 and rides on the cam. When the footprint of scanning beam 14 is at the center of image plane 16, as shown in FIG. 5a, collimator 12 is closest to focal spot 10, and the cross-section of scanning beam 14 is at a maximum. When the footprint of scanning beam 14 is at the edge of image plane 16, as shown in FIG. 5b, collimator 12 is furthest from focal spot 10, and the cross-section of scanning beam 14 is at a minimum. The curvature of cam surface 32a is such that the footprint remains substantially constant throughout a scanline.

Figure 6:
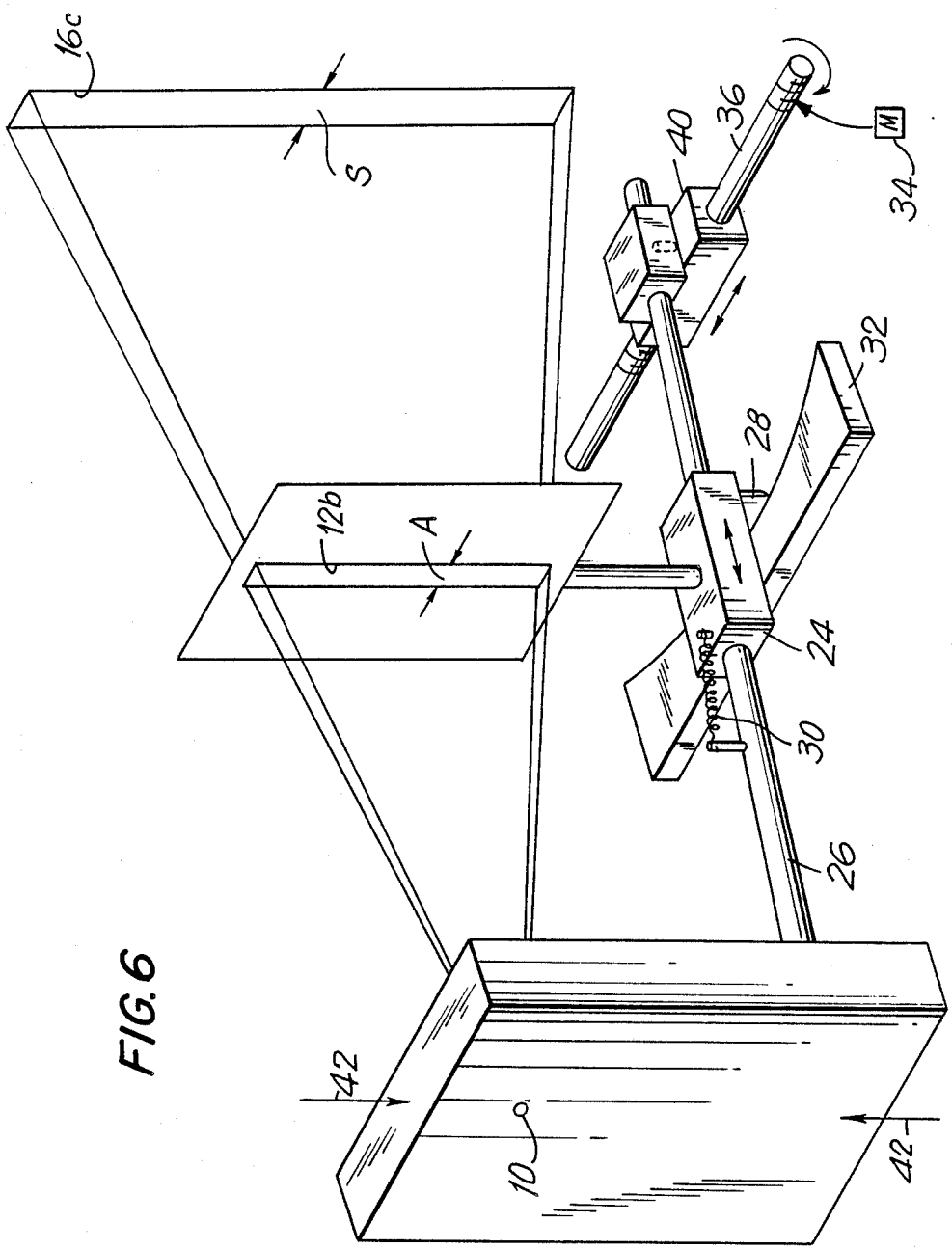
FIG. 6 is a perspective view of a scanning mechanism implementing the embodiment of FIG. 4.

Referring to the perspective view of FIG. 6, like elements bear the reference numerals used in FIGS. 4-5b. The mechanism for scanning footprint 16c along image plane 16 includes, in addition to the earlier-described elements, a motor 34 which drives a lead screw 36 at a constant angular velocity during the travel of footprint 16c along a scan line in image plane 16. Shaft 26 is slidably supported in a linear bearing 38 which in turn is pivotally supported by a nut 40 threaded on lead screw 36 to be driven thereby along the lead screw axis. Lead screw 36 is suitably journaled on bearings which are not 10 shown to maintain its position in space while collimator 12 scans along curved path 22. Similarly, guide 32 is held fixed in space by suitable supports which are not shown, such that aperture 12b in collimator 12 travels in the manner illustrated in FIG. 4.

The curvature of surface 32a can be in accordance with the following relationships, where the coordinates of the center of aperture 12c are X,Y, A is the width of the aperture, S is the footprint width in image plane 16, D is the distance from focal spot 10 to image plane 16 and $\theta$ is the angle of scanning beam 14 relative to the optical axis: $X = \{A/(2S \cos \theta)\}\{D + [D^2 + (S \sin(2\theta)/2)^2]^{\frac{1}{2}}\}$
$Y = \{(A \sin \theta)/(2S \cos^2 \theta)\}\{D + [D^2 + (S \sin(2\theta)/2)^2]^{\frac{1}{2}}\}$ For small angle theta these relationships reduce to:
$X = \{AD/(S \cos \theta)\}$
$Y = \{(AD \sin \theta)/(S \cos^2 \theta)\}$ It is noted that the geometry described above ensures that nut 40 moves at a constant linear velocity but shaft 26 rotates about pivot axis 42—42 at a varying angular velocity in the fashion needed to cause footprint 16c to traverse image plane 16 at a constant linear velocity along a scan line. This constant linear velocity along a scan line can simplify the implementation of schemes for modulating selected parameters of scanning beam 14, as discussed in said copending commonly owned patent application.

It is appreciated that there may be some variation in footprint in the vertical direction. However, it is believed that in the normal case this does not significantly impair the image.

I claim:

1. An x-ray machine comprising:
   a source emitting x-rays toward an object position from a first side of said object position;
   an image plane located at the a second side of said object position;
   a fore collimator system interposed between said source and said object position, said fore collimating system collimating said x-rays to a scanning beam which scans the image plane and changes its cross-sectional area during the scan to maintain a substantially constant footprint of said scanning beam on the image plane.

2. An x-ray machine as in claim 1 in which said fore collimator system comprises an apertured plate which more relative to the source to scan the image plane with said scanning beam, said apertured plate maintaining substantially the same angle with respect to said scanning beam but said apertured plate changing its distance from said source during said scan.

3. An x-ray machine as in claim 2 in which said source has a focal spot from which said x-rays emanate, and in which said fore collimator system comprises a shaft to which the apertured plate is secured for sliding movement along said shaft, wherein said shaft pivots about an axis passing through said focal spot while the apertured plate moves along said shaft to effects said scan.

4. An x-ray machine as in claim 3 in which said fore collimator system comprises a curved guide which is fixed with respect to said source and a bearing which is fixed with respect to said apertured plate and rides on said curved guide to thereby guide the apertured plate along said shaft.

5. An x-ray machine as in claim 4 in which said image plane is flat.

6. An x-ray machine as in claim 5 in which said footprint scans said image plane along respective scanlines and moves at a substantially constant speed along each of said scanlines.

7. A method comprising:
   scanning an object position with a scanning x-ray beam; and
   varying the cross-section of said scanning x-ray beam during the scan to keep substantially constant the beam footprint on an image plane which receives said beam after said beam passes through said object position.

8. A method as in claim 7 in which said scanning step comprises forming said scanning beam by collimating the radiation from an x-ray source with a fore collimator and moving said collimator relative to said source and to said image plane in a scanning motion.

9. A method as in claim 7 in which said varying step comprises moving said fore collimator along a curved path such that said fore collimator is further from said x-ray source at the ends of said curved path than at the center of said curved path.

10. A method as in claim 9 in which said varying step further comprises using an apertured plate as a part of said fore collimator, said apertured plate having an aperture through which said scanning beam passes, and changing the angle of said apertured plate relative to said beam in the course of said scanning of said beam.

* * * * *